United States Patent [19]

Bakke

[11] Patent Number: 5,013,889
[45] Date of Patent: May 7, 1991

[54] ELECTRIC BLOOD WARMER UTILIZING HEATING BY CONDENSATION

[76] Inventor: Allan P. Bakke, 609 19th Ave., S.W., Rochester, Minn. 55902

[21] Appl. No.: 461,532

[22] Filed: Jan. 5, 1990

Related U.S. Application Data

[63] Continuation-in-part of Ser. No. 367,182, Jun. 16, 1989, abandoned.

[51] Int. Cl.⁵ ............................................... H05B 3/20
[52] U.S. Cl. .................................... 392/470; 392/401; 392/403
[58] Field of Search ............... 219/302, 325, 326, 439, 219/462, 524, 525, 530, 540

[56] References Cited

U.S. PATENT DOCUMENTS 3,879,599  4/1975  Kodaira ................. 219/326

Primary Examiner—Bruce A. Reynolds
Assistant Examiner—Tu Hoang

[57] ABSTRACT

An apparatus for warming refrigerated blood to physiologic temperature during transfusion at flow rates from zero to greater than 160 milliliters per minute. The apparatus consists primarily of two hollow metal rectangular box shaped heating units containing a water reservoir in equilibrium with a larger volume of water vapor. Heat is applied to the water reservoir, generating steam which condenses on one wall of each heating unit serving as a heating plate. Heat is then transferred by conduction to a thin metal cartridge or plastic pouch type conduit sandwiched between the two heating plates. Very high heat transfer coefficients maintain heating plates at constant temperature without the possibility of damage to blood by local overheating.

19 Claims, 5 Drawing Sheets

ELECTRIC BLOOD WARMER UTILIZING HEATING BY CONDENSATION

This is a continuation-in-part of application Ser. No. 07/367,182, filed June 16, 1989 now abandoned.

BACKGROUND—FIELD OF INVENTION

The present invention generally relates to devices for heating liquids, and more particularly to an electric blood warmer utilizing nucleate boiling and heating by film condensation at subatmospheric pressure characterized by accurate temperature control and very high heat transfer rates, capable of heating blood or other fluids for infusion from refrigerated storage temperature to physiologic temperature at flow rates varying from zero to those required for massive transfusion. The present invention also relates to a device for heating or thawing physiologic or other fluids at high heat transfer rates without the possibility of subjecting the heated fluid to locally excessive temperatures.

Blood is generally stored at a temperature near 4° C. Prior to intravenously infusing refrigerated blood into the human body, it should be warmed to near physiologic temperature (32° to 37° C.) During massive transfusions flow rates of 160 milliliters per minute or more may be required.

1. Background—Cross-Reference to Related Applications

This Application is related to the following pending (now issued) patent application.

| | |
|---|---|
| Appn. Number | 07/132,193 |
| Filing Date | December 14, 1987 |
| Applicant | Allan P. Bakke |
| Title | Ribbon-Flow Cartridge-Type Dry Heat Blood Warmer |

The above pending application was allowed and issued as follows, before submission of the present continuation-in-part application.

| | |
|---|---|
| U.S. Pat. No. | 4,847,470 |
| Date of Issue | July 11, 1989 |
| Title | Electric Blood Warmer Utilizing Metallic Ribbon Flow Cartridge and Low Thermal Mass Heating Units |
| Inventor | Allan P. Bakke |

2. Background—Description of Prior Art

Various kinds of blood warmers presently exist. Most utilize a flexible plastic container or conduit for the blood being heated, such as plastic tubing immersed in a warm water bath or a plastic bag or pouch sandwiched between heating plates. Heating plates are usually electrical resistance heaters. Cold blood entering the warmer at a high flow rate would suggest higher heat transfer rates decreasing as an aliquot of blood approaches the outlet of the warmer. At low or zero flow rates, however, a high heating rate near the inlet overheats locally causing hemolytic destruction of erythrocytes.

The related U.S. Pat. No. 4,847,470 utilizes etched foil heaters with uniform heating rates, low thermal mass heating plates, and points out the potential benefits of multistage heating, which approaches the constant wall temperature heat transfer model.

SUMMARY OF THE INVENTION

The present invention provides the benefits of a multistage heater with a very large number of stages, by providing essentially constant temperature (37° C.) of the heating plates.

The present invention employs two heating units. One flat wall of each is called a heating plate. Between the two heating plates is sandwiched a metallic ribbon-flow cartridge through which blood flows while being warmed. A plastic pouch-type conduit would also benefit from this type heat source. One heating unit is fixed and the other movable, allowing easy insertion, clamping, and removal of the cartridge or pouch.

Each heating unit is comprised of a sealed metal rectangular box containing approximately one fourth of its volume as a reservoir of water above which is pure water vapor. This water—water vapor system has predictable thermodynamic states relating temperature and pressure, and pressure at 37° C. is very low (vacuum) about 1 psi absolute.

Heat is applied to the outside of the metal box heating unit in the region of the water reservoir indicator-controller by etched foil electric heaters, raising the temperature of the water (and of the water vapor in equilibrium above it). Water temperature is controlled by one commercially available temperature indicator-controller for each of the two heating units, providing redundancy of performance upon the failure of one heating unit.

To achieve high rates of vapor production, the heated evaporator region walls may need to be several degrees warmer than the vapor produced; this difference is termed excess temperature.

Water vapor (steam) condenses on the only slightly cooler internal walls of the heating plates, and heat is transferred to the blood with very a high heat transfer coefficient of approximately 2800 BTU/(hr ft °F.). Heating plate temperature is maintained at approximately 37° C. from inlet to outlet. Steam is generated as needed by nucleate boiling in the heated water reservoir evaporator region.

The present invention provides redundancy in performance through the use of two separate and independent heating and control systems for the two heating units. The two heating units heat opposite sides of the disposable cartridge or plastic pouch sandwiched between them, through which blood flows while being heated.

A separate overtemperature thermostat, independent of the temperature indicator-controller system, is provided for each heating unit and breaks its heater circuit if outlet plate temperature exceeds a safe limit for blood of approximately 44° C.

The very high heat transfer coefficient achieved by film condensation of water vapor provides an essentially constant heating plate temperature which assures maximal heat transfer to the blood without the possibility of local overheating and hemolysis of blood cells. This constant wall temperature condition is equivalent to utilizing a very large number of temperature sensors and heater controllers along the path of blood as it flows from inlet to outlet of the warming cartridge or pouch.

Another embodiment of the present invention utilizes capillary action occurring in a porous wick material mat approximately 1/16 inch thick in intimate contact with the inner walls of the heating plate and also the inner walls of the region of the heating unit to which heat is supplied by the electric etched foil heaters to produce vapor. The porous wick material mat forms a continuous capillary flow path to return condensed vapor condensate to the electrically heated evaporator region by capillary action. Capillary action in the porous mat also serves to maintain a thin layer of liquid for vapor production on the inner walls of the evaporator region. Only a small depth (approximately ⅛ inch) of liquid need be maintained in the dependent portion of the evaporator region, reducing the overall blood warmer weight. The porous mat also provides a large surface area for evaporation, thus reducing the excess temperature (temperature of the evaporator wall minus the vapor temperature) necessary for high rates of vapor production.

Accordingly, the present invention relates to an apparatus for warming blood or any fluid with zero to very high heat transfer and/or flow rates and requiring very closely controlled temperatures, and consists primarily of two rectangular, sealed metal heating units containing water and water vapor in equilibrium. Controlled temperature subatmospheric vapor production and film condensation on the heating plate inner wall provide very high heat transfer capability without the possibility of local overheating because vapor and the water reservoir are at the same temperature. If any point on the condensing surface reaches the steam temperature, zero heat transfer obtains.

DESCRIPTION OF THE PREFERRED EMBODIMENT

Figure 1:
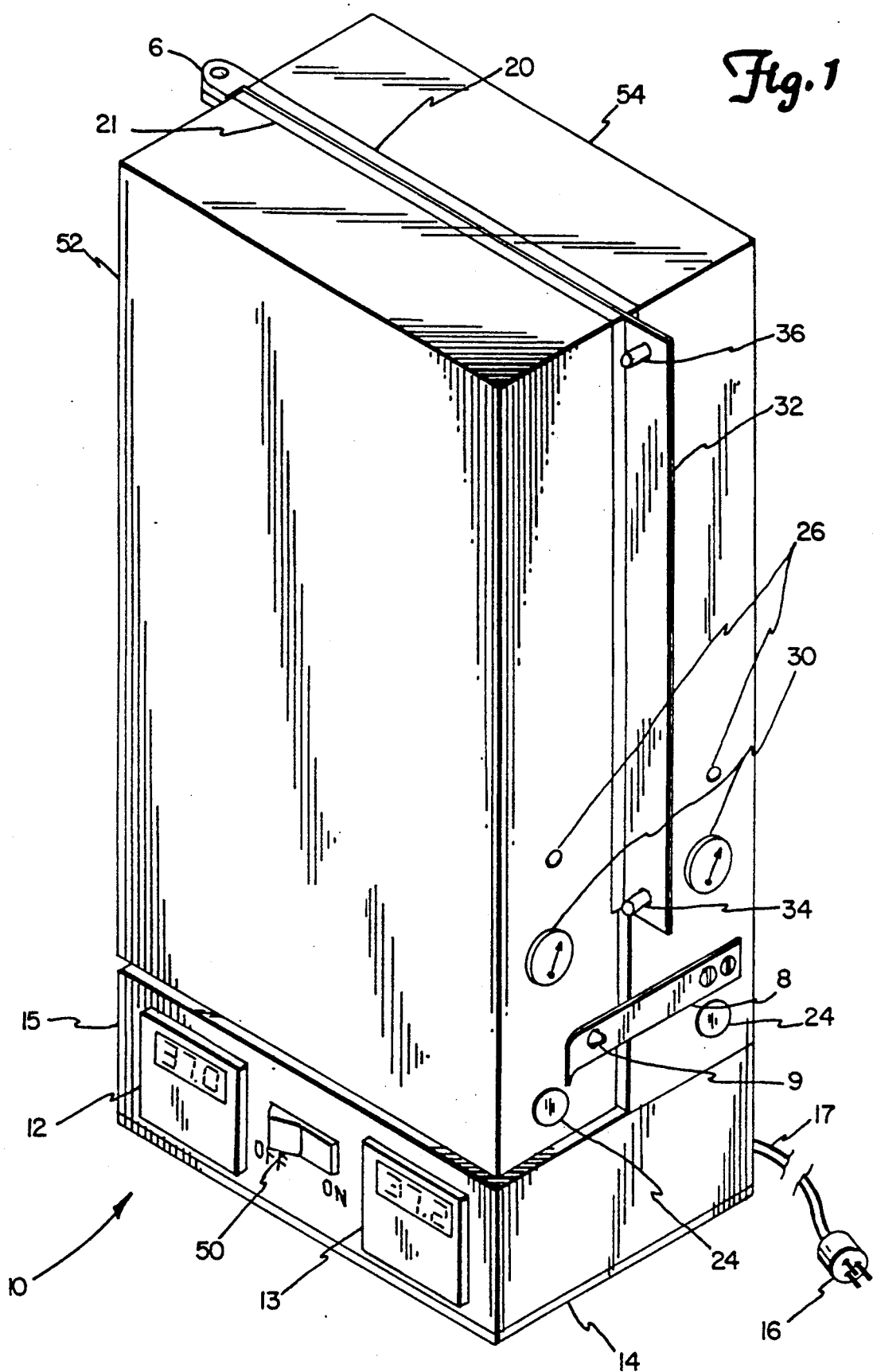
FIG. 1 is an isometric front view of the preferred embodiment of the present invention, an electric blood warmer utilizing heating by condensation.

Referring now to the drawings, and more particularly to FIG. 1, there is shown an electric blood warmer utilizing heating by condensation apparatus, generally designated warmer apparatus 10, which comprises the preferred embodiment of the present invention. The apparatus 10 includes a base 14 which allows apparatus 10 to rest on a flat surface with great stability. The housing 15 is securely attached to base 14 and serves to mechanically support and enclose temperature indicator-controllers 12 and 13 and on-off switch 50.

Referring again to FIG. 1, disposable blood warming cartridge 32 is sandwiched snugly between fixed heating unit 54 and movable heating unit 52. Movable heating unit 52 pivots to open and close on hinges 6 and is retained in the closed position by spring latch 8 engaging latch pin 9.

Figure 2:
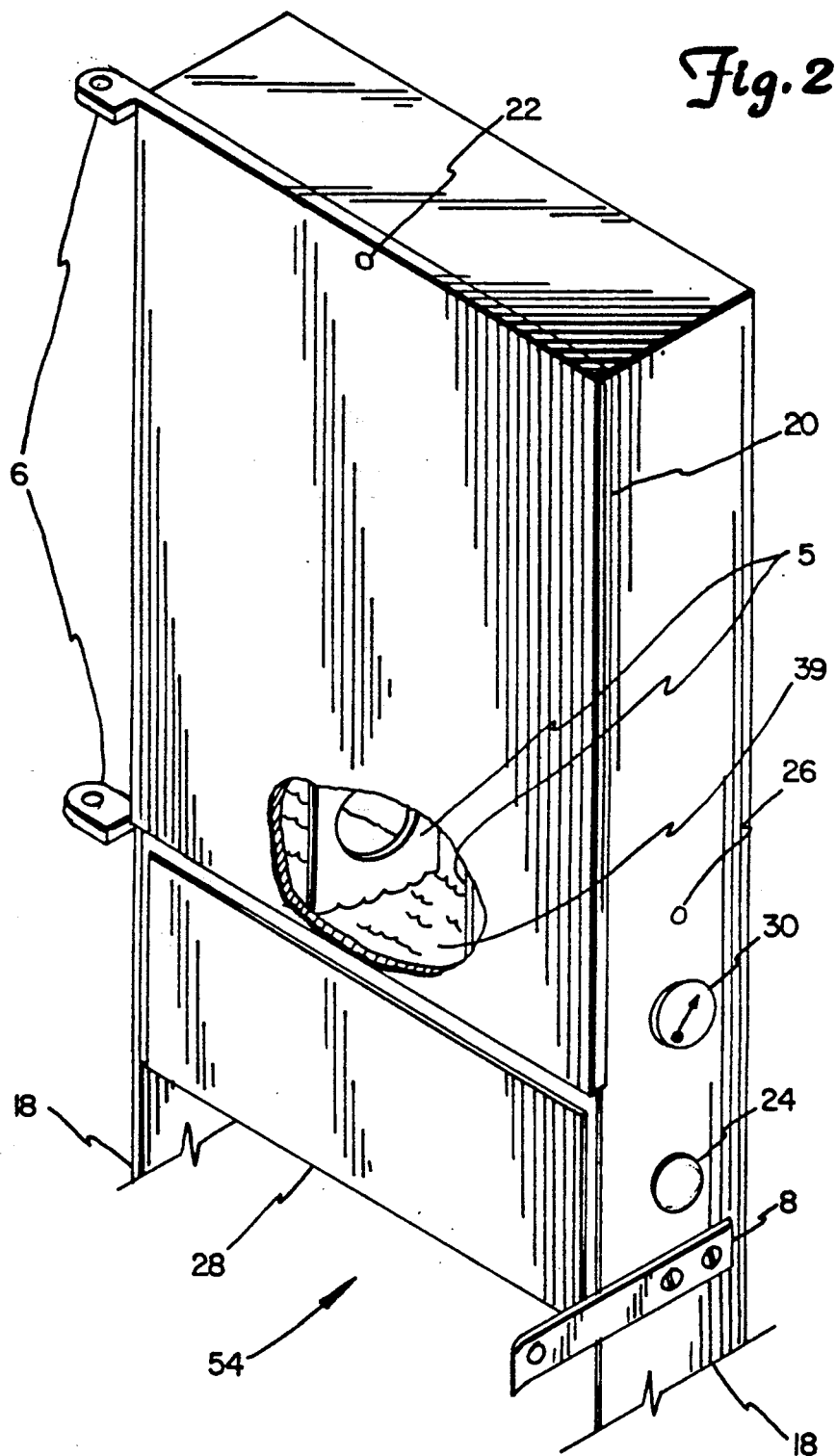
FIG. 2 is a partially sectioned isometric view of the fixed heating unit.

Referring to FIG. 2, fixed heating unit 54 is shown in detail, and is constructed of aluminum sheet or other metal. Movable heating unit 52 is functionally identical to 54. Vacuum gage 30 confirms at a glance that the hermetically sealed heating unit is intact and has not in-leaked atmospheric air. Water temperature sensor 26 is a thermocouple or resistive temperature device (RTD) which provides input to temperature indicator-controller 12. Vacuum tight fusible plug 24 protects against positive internal pressure and attendant risk of rupture if heating were continued despite all other safety devices. If temperature of water 39 exceeds approximately 70° C., fusible plug 24 melts preventing internal pressure build-up (system pressure would remain subatmospheric until water temperature approaches 100° C.).

Again referring to FIG. 2, etched foil electric heater 28 is vulcanized or bonded to outside of water reservoir evaporator region of heating unit 54, i.e. to outer surface of heating unit below water level. Heating plate 20 is heated internally by condensing steam and transfers heat by conduction to blood contained in and traversing blood warming cartridge 32 of FIG. 1. Internal stiffeners 5 provide mechanical support to the heating unit walls against external atmospheric pressure. Fixed heating unit support legs 18 support fixed heating unit 54 mechanically and are firmly secured to housing 15 and base 14.

Figure 3:
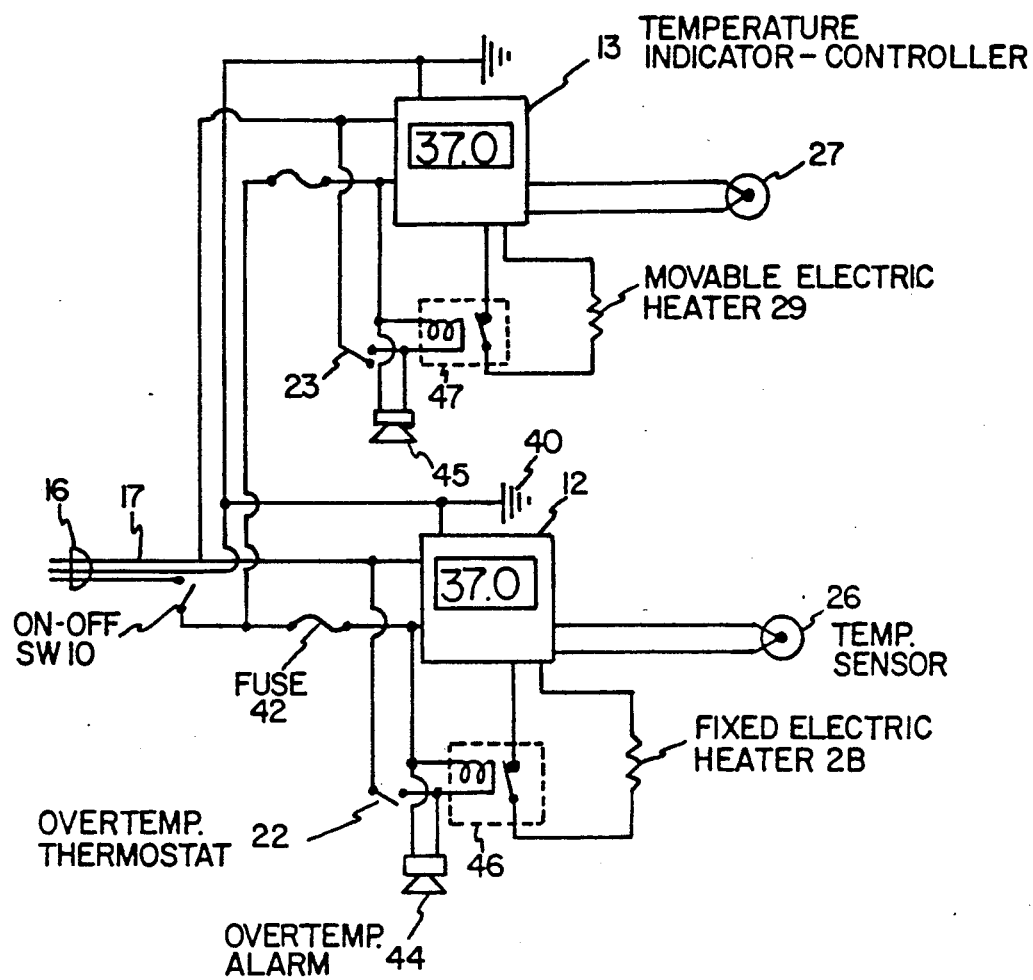
FIG. 3 is a schematic diagram of the electrical circuits and elements employed in the present invention.

FIG. 3 is a schematic diagram of the electrical components and wiring of the apparatus 10. There are two functionally independent temperature indicator-controllers 12 and 13 for the fixed and movable heating units 54 and 52 respectively. Grounded plug 16, connected to power cord 17 provides 110 volt, 60 Hz power obtained from a grounded wall source. On-off switch 50 interrupts power to the apparatus 10 by choice of the operator. Fuse 42 opens the power supply circuit if excessive current flows. Ground 40 connects electrically to housing 15 and to the ground connection of temperature indicator-controllers 12 and 13, which are commercially available devices with digital temperature display, employing on-off or proportional band control of electrical etched foil heaters 28 and 29 with zero crossing electronic switching of a triac to control the supply of power to heaters 28 and 29. Temperature sensors 26 and 27 are used to measure temperature of the water vapor regions. Controllers 12 and 13 maintain their respective water—water vapor systems temperatures at approximately 37° C. by appropriately energizing heaters 28 and 29. Failure of sensor 26 or 27 results in and "upscale" or high temperature indication, internal alarm, and shutoff of electric heaters 28 or 29 by controller 12 or 13.

A completely separate safety shutoff for excessive temperature is comprised of overtemperature thermostats 22 and 23 which are in thermal contact with the outlet region of heating plates 20 and 21 respectively, overtemperature relay switches 46 and 47, and overtemperature alarms 44 and 45. Overtemperature thermostat 22 or 23 closes at a preset temperature known to be safe for blood (approximately 44° C.), energizing both alarm 44 or 45 and relay switch 46 or 47 which interrupts power to heater 28 or 29.

Figure 4:
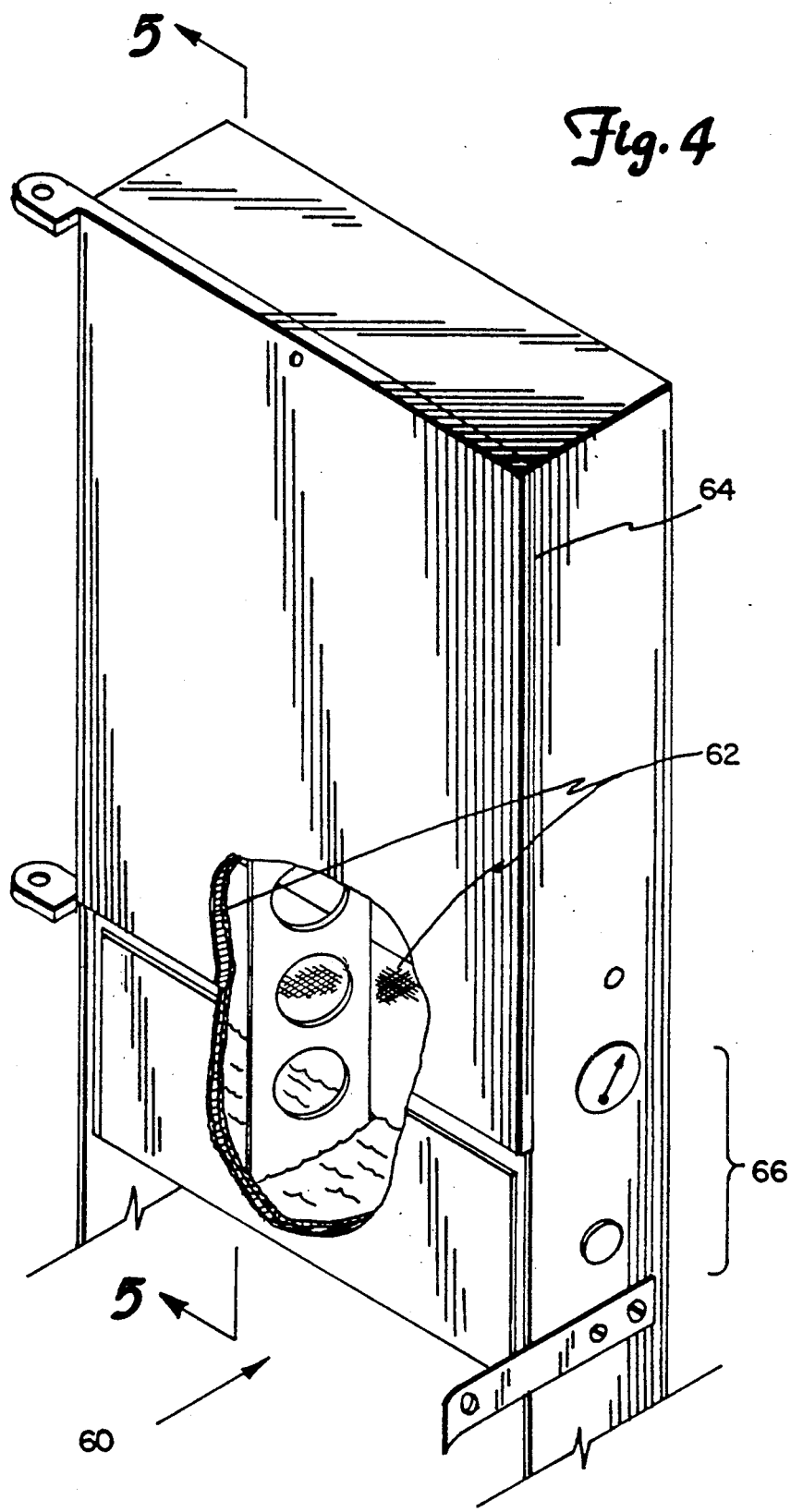
FIG. 4, is a partially sectioned isometric view of an alternative embodiment of the fixed heating unit utilizing capillary action in a porous wick material mat.
Figure 5:
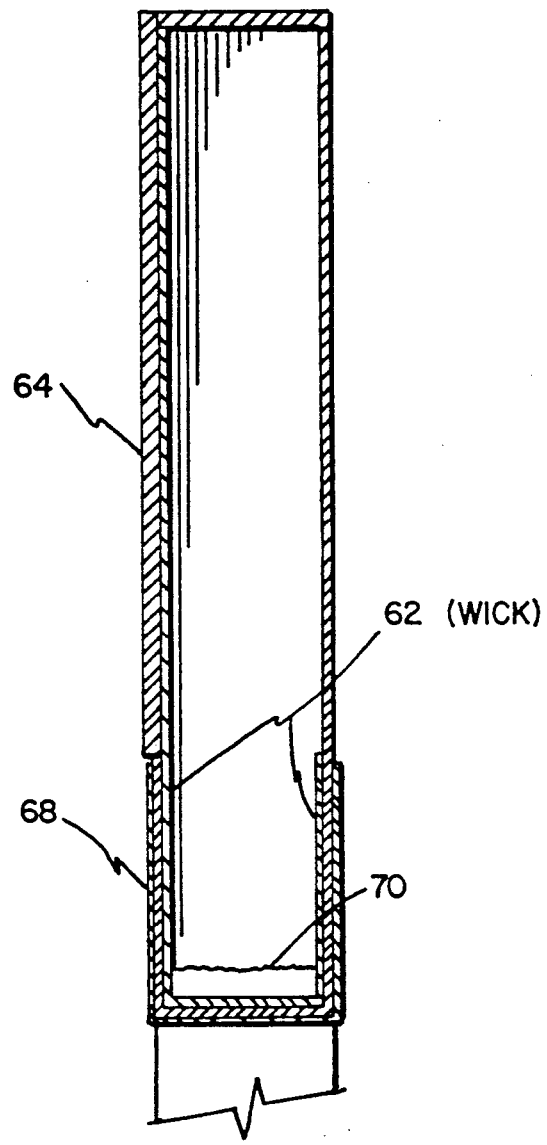
FIG. 5 is a sectional view of the fixed heating unit of FIG. 4.

Another embodiment of the present invention is shown in FIG. 4 and FIG. 5. A porous wick material mat 62 approximately 1/16 inch thick is affixed to or otherwise held in intimate contact with the interior walls of fixed heating unit 60 covering the region of heating plate 64 and evaporator region 66. Mat 62 may be made of metal mesh, fiberglass or other material. Steam condensing on the mat in the region of the heating plate produces liquid water which is returned to evaporator region 66 by capillary action. Capillary action also maintains a thin layer of liquid water on the inner walls of evaporator region 66 for vapor production when etched foil heaters 68 are energized, allowing water reservoir 70 to be a small volume, approximately 1/8 to 1/4 inch deep. The large surface area of the porous wick material mat enhances evaporation and thus reduces the excess temperature (evaporator surface temperature minus vapor temperature) required for high rates of steam production.

In operation cold blood under slight pressure enters cartridge 32 at inlet 34, then spreads out and flows as a thin layer through cartridge 32 and exits through outlet 36 and the warmed blood is infused intravenously.

The heating units are preferably about 15 inches to 16 inches high, about 6 inches to 8 inches wide, and about 2 inches deep with the metal wall thicknesses being about 1/8 inch thick. The heating plate portions 20 of the heating units are about 6 inches to 8 inches wide, 11 inches to 12 inches high, and about 1/8 inch to 1/4 inch thick. The reservoir in the bottom of the heating unit contains liquid to a depth of about 4 inches, about 60 cubic inches in volume, in the absence of wicking. When wicking is present the reservoir need only be about 1/4 inch to 1/2 inch deep having a volume of about 6 cubic inches. Foil heaters 28 have a thickness of about 0.02 inches and cover a surface area of about 50 to 70 square inches. They are rated to produce heat at a power density of about 10 to 20 watts per square inch. Fusible plugs 24 are about 1/2 inch in diameter, and are made of a metal having a predictable melting temperature of about 60 to 70 degrees C. Wicking material 62 is about 1/16 inch thick to maintain a liquid layer about 0.04 inch thick on the interior walls of the heating unit.

From the foregoing description, it will be apparent that the invention disclosed herein provides a novel and advantageous blood warmer design. As will be understood by those familiar with the art, the invention may be embodied in other specific forms without departing from the spirit or essential characteristics thereof. For example, another liquid-vapor system other than water might be used, and the invention may be applied to another heating process requiring accurate control of warming temperatures and/or widely variable heating rates.

I claim:

1. An apparatus for warming blood for transfusion comprising:
   (A) at least one heating unit including:
      (1) a rigid metal housing having walls, vertically disposed, enclosing a hermetically sealed air-free space having a lower liquid phase evaporation region containing an evaporatable liquid and an upper vapor phase condensation region, one flat wall adjacent said condensation region functioning as a heating plate by transferring heat from vapor therein,
      (2) external etched foil electric heating means adjacent said evaporation region for generating vapor from said liquid, and
      (3) temperature sensing means adjacent said condensation region for sensing the temperature of vapor therein,
   (B) means for connecting said etched foil electric heating means to a source of electric power,
   (C) control means responsive to said temperature sensing means to control the amount of heat supplied by said eldered foil electric heating means to said heating unit liquid phase evaporation region, and
   (D) means for passing blood in conductive heat transference contact with said heating plate.

2. An apparatus according to claim 1 wherein said heating unit utilizes water as said liquid.

3. An apparatus according to claim 1 wherein said heating unit further includes vacuum gage means for indicating vacuum inside said enclosed hermetically sealed space, and a vacuum tight fusible plug in one of its walls, said plug being made of a metal with a predictable melting temperature of about 60 to 70 degrees C.

4. An apparatus according to claim 1 wherein:
   (A) said heating unit comprises:
      (1) a vertically disposed rectangular wall,
      (2) a liquid reservoir in the evaporation region of said heating unit, and
      (3) a flat heating plate forming the upper portion of one of the heating unit in the condensation region of said heating unit, and
   (B) said means for passing blood in heat transference contact with said heating plate comprises a flat heatable blood warming cartridge or pouch disposed to be clamped against said heating plate and be heated thereby.

5. An apparatus according to claim 4 wherein:
   (A) said rectangular wall of the heating unit is about 15 to 16 inches high, 6 inches to 8 inches wide, and 2 inches deep with said metal walls generally about 1/8 inch to 1/4 inch thick, and
   (B) said heating plate is about 6 inches to 8 inches wide, and 11 inches to 12 inches high.

6. An apparatus according to claim 5 wherein said liquid reservoir is about 60 cubic inches in volume and fills in said heating unit to a depth of about 4 inches.

7. An apparatus according to claim 6 wherein said heating means comprises an etched foil electric heater bonded to the outer surface of said liquid reservoir in the evaporation region of said heating unit.

8. An apparatus according to claim 7 wherein said etched foil heater is approximately 0.02 inches thick, covers a surface area of about 70 square inches, and is rated to produce heat at a power density of about 10 to 20 watts per square inch.

9. An apparatus according to claim 1 wherein said heating unit further includes:
   (A) means for returning liquid condensate from the condensation region to the evaporation region by capillary action, and
   (B) means for maintaining a thin layer of liquid on the interior wall of heating unit at said evaporation region by capillary action.

10. An apparatus according to claim 9 wherein said means for returning and maintaining liquid condensate comprises a porous fibrous wick mat fixed in intimate contact with and covering the interior surface of said heating unit.

11. An apparatus according to claim 10 wherein said liquid reservoir is about 6 cubic inches in volume and fills in said heating unit to a depth of about 1/4 inch to 1/2 inch.

12. An apparatus according to claim 11 wherein said heating means comprises an etched foil electric heater bonded to the outer surface of said liquid reservoir evaporation region wall at said heating unit.

13. An apparatus according to claim 12 wherein said etched foil heater is approximately 0.02 inches thick, covers a surface area of about 50 square inches, and is rated to produce heat at a power density of about 10 to 20 watts per square inch.

14. An apparatus according to claim 10 wherein said porous fibrous wick mat is about 1/16 inch thick.

15. An apparatus according to claim 4 wherein said apparatus comprises:
(A) a first fixed heating unit,
(B) a similar movable heating unit hingedly supported by said first unit, the flat heating plate of each said heating units being in parallel facing and closely spaced apart relation, and
(C) latch means for releasably clamping a flat blood warming cartridge or pouch therebetween.

16. An apparatus for warming blood for transfusion comprising:
(A) a first fixed heating unit including:
  (1) a rigid metal housing having walls vertically disposed enclosing a hermetically sealed air-free space having a lower liquid phase evaporation region containing a reservoir of evaporatable liquid, and an upper vapor phase condensation region, one flat wall adjacent said condensation region functioning as a heating plate by transferring heat from vapor therein,
  (2) external electric heating means adjacent said evaporation region for generating vapor from said liquid, and
  (3) temperature sensing means adjacent said condensation region for sensing the temperature of vapor therein,
(B) a similar second movable heating unit hingedly supported by said first unit, the flat heating plate of each said heating units being in parallel facing and closely spaced apart relation, and
(C) latch means on said heating unit for releasably clamping a flat blood warming cartridge or pouch therebetween,
(D) means for connecting said heating means to a source of electric power, and
(E) control means responsive to said temperature sensing means to control the amount of heat supplied by said heating means to said heating unit liquid phase evaporation regions.

17. An apparatus according to claim 16 wherein each of said heating units utilize water as said liquid.

18. An apparatus according to claim 16 wherein said heating units each further include vacuum gage means for indicating vacuum inside said enclosed hermetically sealed space, and a vacuum tight fusible plug in one of its walls, said plug being made of a metal with a predictable melting temperature of about 60 to 70 degrees C.

19. An apparatus according to claim 16 wherein each of said heating units further include:
(A) a porous fibrous wick mat fixed in intimate contact with and covering the interior surface of said heating plate for returning liquid condensate from the interior wall of the condensation region to the evaporation region by capillary action, and
(B) a porous fibrous wick mat fixed on the interior wall of said evaporation region for maintaining a thin layer of liquid thereon by capillary action.

* * * * *